(12) United States Patent
Mande et al.

(10) Patent No.: US 12,383,599 B2
(45) Date of Patent: Aug. 12, 2025

(54) SYSTEM AND METHOD FOR COMBATING INFECTIONS DUE TO ANTIBIOTIC INDUCED PATHOGENS

(71) Applicant: Tata Consultancy Services Limited, Mumbai (IN)

(72) Inventors: Sharmila Shekhar Mande, Pune (IN); Swadha Anand, Pune (IN); Preethi Alagarai Sampath, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 792 days.

(21) Appl. No.: 17/596,180

(22) PCT Filed: Jun. 5, 2020

(86) PCT No.: PCT/IB2020/055305
§ 371 (c)(1),
(2) Date: Dec. 3, 2021

(87) PCT Pub. No.: WO2020/245781
PCT Pub. Date: Dec. 10, 2020

(65) Prior Publication Data
US 2022/0233637 A1 Jul. 28, 2022

(30) Foreign Application Priority Data
Jun. 6, 2019 (IN) .............................. 201921022521

(51) Int. Cl.
| | | |
|---|---|---|
| C12N 15/70 | (2006.01) | |
| A61K 31/7088 | (2006.01) | |
| A61K 38/16 | (2006.01) | |
| A61K 38/46 | (2006.01) | |
| C12N 15/10 | (2006.01) | |
| C12Q 1/689 | (2018.01) | |

(52) U.S. Cl.
CPC ........ *A61K 38/164* (2013.01); *A61K 31/7088* (2013.01); *A61K 38/465* (2013.01); *C12N 15/1072* (2013.01); *C12Q 1/689* (2013.01); *C12Q 2600/158* (2013.01)

(58) Field of Classification Search
CPC .......... Y02A 50/30; A61K 35/74; C12N 1/20; C12N 9/22; C12N 15/70; C12N 15/09; C12N 2710/24062; C12N 2800/101; C12Q 1/689; C12Q 2600/16; C12Q 1/6806; C12Q 1/6851; C12P 19/34; C12P 1/04; C12P 39/00
USPC ...................................................... 435/69.1
See application file for complete search history.

(56) References Cited

U.S. PATENT DOCUMENTS

| | | |
|---|---|---|
| 8,906,635 B2 | 12/2014 | Jin et al. |
| 2012/0282274 A1 | 11/2012 | Jin et al. |
| 2014/0315985 A1 | 10/2014 | May et al. |
| 2015/0353901 A1 | 12/2015 | Liu et al. |
| 2018/0371405 A1 | 12/2018 | Barrangou et al. |

FOREIGN PATENT DOCUMENTS

EP 2252702 B1 1/2014

OTHER PUBLICATIONS

Kisselev L., Structure, 2002, vol. 10: 8-9.*
Kwiatkowski et al., Biochemistry 38:11643-11650, 1999.*
Wristlock et al., (Quarterly Reviews of Biophysics 2003, vol. 36 (3): 307-340.*
Davos et al., (Proteins: Structure, Function and Genetics, 2000, vol. 41: 98-107.*
Raquel Tobes et al. et al, "Bacterial repetitive extragenic palindromic sequences are DNA targets for Insertion Sequence elements", Research Article, Mar. 2006, BMC Genomics, https://bmcgenomics.biomedcentral.com/track/pdf/10.1186/1471-2164-7-62.pdf.
International Search Report and Opinion mail dated Jul. 22, 2021, for International Application No. PCT/IB20/55305, filed Jun. 5, 2020. 12 pgs.
GenBank Accession No. CP013217, *Kurthia* sp. 11 kri321, complete genome, Jan. 25, 2016 [online]. [Retrieved on Jun. 28, 2021]. Retrieved from the internet at <URL: https://www.ncbi.nlm.nih.gov/nuccore/CP013217>.
GenBank Accession No. LR535851, *Mastacembelus armatus* genome assembly, chromosome: 19, Mar. 14, 2019 [online]. [Retrieved on Jun. 28, 2021]. Retrieved from the internet at <URL: https://www.ncbi.nlm.nih.gov/nuccore/LR535851 >.
GenBank Accession No. GO192826, CAGB13772.fwd CAGB *Alvinella pompejana* Normalized 1-16, 24 library RN05 posterior end *Alvinellapompejana* cDNA clone CAGB13772 5', mRNA sequence, Feb. 19, 2009 [online]. [Retrieved on Jun. 28, 2021]. Retrieved from the internet at <URL: https://www.ncbi.nlm.nih.gov/nuccore/GO192826>.

* cited by examiner

*Primary Examiner* — Tekchand Saidha
*Assistant Examiner* — Mohammad Y Meah
(74) *Attorney, Agent, or Firm* — Finnegan, Henderson, Farabow, Garrett & Dunner, LLP

(57) ABSTRACT

Nosocomial infections are a major threat to the health sector. A specific category of these are the infections caused by antibiotic induced susceptibility to various pathogenic bacteria. This disclosure relates generally to method and system for combating infections due to antibiotic induced pathogens. The system provides strategies to combat pathogenic infections caused by multi-drug resistant (MDR) and extensively drug resistant (XDR) strains of antibiotic induced pathogens. The idea used in this disclosure utilizes the fact that multiple occurrences of a conserved stretch of nucleotide sequence on a pathogen genome and surrounded by genes encoding virulence factors or which are in vicinity of genes essential for survival of the candidate pathogen can be targeted to disrupt the overall genetic machinery of the pathogen. The present disclosure has been explained on sequenced genomes of *Clostridium difficile* and vancomycin-resistant *Enterococcus* sp.

18 Claims, 7 Drawing Sheets

Specification includes a Sequence Listing.

*Clostridium difficile*/VRE genome

— RCLOS/RENT-FL/RENT-FM
— Virulent / essential genes

FIG. 2

```
                          200
                           ↘         ( Start )
                                         ↓
              ┌─────────────────────────────────────────────────┐
              │        Obtain a sample from an infected area     │─── 202
              └─────────────────────────────────────────────────┘
                                         ↓
              ┌─────────────────────────────────────────────────┐
              │ Isolate DNA from the obtained sample using one of a laboratory methods │─── 204
              └─────────────────────────────────────────────────┘
                                         ↓
              ┌─────────────────────────────────────────────────┐
              │              Sequence the isolated DNA           │─── 206
              └─────────────────────────────────────────────────┘
                                         ↓
```

┌──────────────────────────────────────────────────────────────────┐
│ Detect presence of the antibiotic induced pathogens, wherein the antibiotic induced │
│ pathogens comprise one or more of *Clostridium difficile*, vancomycin-resistant │
│ *Enterococcus faecalis* and vancomycin-resistant *Enterococcus faecium* from the │── 208
│                    isolated DNA of the sample                    │
└──────────────────────────────────────────────────────────────────┘

┌──────────────────────────────────────────────────────────────────┐
│ Prepare and administer an engineered polynucleotide construct on infected area │
│ using a plurality of detection methods to combat the infections due to the antibiotic │
│ induced pathogens, wherein the engineered polynucleotide construct is comprising: │
│ • one or more of a set of nucleotide repeat sequences of multiple copies dispersed │
│   in nucleotide sequences of genomes of one or more of the *Clostridium difficile*, │
│   vancomycin-resistant *Enterococcus faecalis* and vancomycin-resistant │
│   *Enterococcus faecium* genomes, wherein the set of nucleotide sequences with │── 210
│   repeats comprises one or more of a Sequence ID 001, a Sequence ID 002, a │
│   Sequence ID 003, complement of the Sequence ID 001, complement of the │
│   Sequence ID 002 or complement of the Sequence ID 003, │
│ • a first enzyme capable of nicking & cleaving set of nucleotide sequences, and │
│ • a second enzyme capable of removal of a set of neighborhood genes flanking the │
│   set of nucleotide sequences with repeats │
└──────────────────────────────────────────────────────────────────┘

┌──────────────────────────────────────────────────────────────────┐
│ Check the efficacy of the administered engineered polynucleotide construct to │── 212
│    combat the antibiotic induced pathogens after a predefined time period        │
└──────────────────────────────────────────────────────────────────┘

┌──────────────────────────────────────────────────────────────────┐
│ Re-administer the engineered polynucleotide construct if the antibiotic induced │── 214
│     pathogens are still present after checking in the infected area              │
└──────────────────────────────────────────────────────────────────┘
                                         ↓
                                     ( Stop )

FIG. 6

SYSTEM AND METHOD FOR COMBATING INFECTIONS DUE TO ANTIBIOTIC INDUCED PATHOGENS

CROSS REFERENCE TO RELATED PATENT APPLICATIONS AND PRIORITY

The present application is a U.S. National Stage Filing under 35 U.S.C. § 371 and claims priority from International Application No. PCT/IB2020/055305, filed on Jun. 5, 2020, which application claims priority from Indian Provisional Patent Application No. 201921022521, filed on Jun. 6, 2019. The entire contents of the aforementioned applications are incorporated herein by reference.

REFERENCE TO SEQUENCE LISTING SUBMITTED ELECTRONICALLY

An official copy of the sequence listing is submitted electronically via EFS-WEB as an ASCII formatted sequence listing with a file named Antibiotic_induced_ST25, created on Mar. 17, 2025, having a size of 1,431 bytes. The sequence listing contained in this ASCII formatted document is part of the specification and is herein incorporated by reference in its entirety.

TECHNICAL FIELD

The embodiments herein generally relate to the field of nosocomial infections, and, more particularly, to a method and system for combating the problem of multi-drug resistance in pathogens causing infections induced due to the consumption of antibiotics in the hospitalized environment.

BACKGROUND

Nosocomial (hospital-acquired) infections are a major threat to the health sector. A specific category of these are the infections caused by antibiotic induced susceptibility to various pathogenic bacteria. These infections occur in patients who are presently on an antibiotic treatment. These pathogens are developing resistance to many classes of antibiotics used during their treatment. Two such pathogens are *Clostridium difficile* and vancomycin-resistant *Enterococcus* sp.

*Clostridium difficile* is associated with antibiotic induced diarrhea in most hospitalized or recently hospitalized patients. It has been shown that a new strain of *Clostridium difficile* has emerged that is resistant to fluoroquinolone antibiotics, which are commonly used to treat infections. This stronger virulent strain is shown to be associated with 400% increase in mortality rate in patients afflicted with the infection. Other equally notorious pathogens in this category are vancomycin-resistant *Enterococcus faecalis* and vancomycin-resistant *Enterococcus faecium*. As the name suggests they are resistant to antibiotic vancomycin which is used as a last resort treatment method. This makes the pathogen extremely difficult to treat with very few treatment options and a very high infection rate. Both *Clostridium difficile* and vancomycin-resistant *Enterococcus* sp., are classified as urgent and serious threats respectively by CDC (Centre of Disease Control and Prevention).

Additional problems arise which pertain to formation of biofilms in these bacteria which allow them to evade antibiotics. Several studies have shown that inhibitors of biofilm formation (like several enzymes which degrade the matrix) as well as quorum quenchers (which prevent biofilm formation) can prove to be useful in this regard. Despite utilizing such inhibitors, several bacteria still escape the antibiotics and lead to relapse of the symptoms once the treatment is stopped. Several side effects and cross-reactivity are observed due to intake of present drugs. Most of the antibiotics land up killing the beneficial human microbiome also.

Majority of the existing methods for combating pathogens focus on silencing or inhibiting function of specific genes in the pathogens in order to curtail their expression. Targeting single functional aspects of infecting bacteria often is not sufficient as these pathogens might mutate their targets and develop resistance to the therapeutic intervention thereby reducing or removing the efficacy of such therapies. This is termed as Antimicrobial Resistance.

SUMMARY

Embodiments of the present disclosure present technological improvements as solutions to one or more of the above-mentioned technical problems recognized by the inventors in conventional systems. For example, in one embodiment the system is provided for combating infections due to antibiotic induced pathogens, the system comprises a sample collection module, a pathogen detection and DNA extraction module, a sequencer, one or more hardware processors, a memory and an administration module. The sample collection module obtains a sample from an infected area. The pathogen detection and DNA extraction module isolates DNA/RNA from the obtained sample using one of a laboratory methods and utilizes experimental methods to detect the pathogen. The sequencer sequences the isolated DNA. The memory in communication with the one or more hardware processors, wherein the one or more first hardware processors are configured to execute programmed instructions stored in the one or more first memories, to: identify a set of nucleotide sequences in the sequenced DNA which repeat more than a predefined number of times, wherein the predefined number of times refers to the occurrence of a nucleotide sequence stretch at least 10 or more times on the pathogen genome, wherein the sequences are corresponding to one or more than one strain of the antibiotic induced pathogens or candidate genus or species, wherein the identified set of nucleotide repeat sequences occur in multiple copies found at distant locations on genomes of all pathogenic strains of candidate genus or specie and these nucleotide repeat sequences do not show more than two matches on nucleotide sequence alignment with genomes of genera or species other than the genomes of the candidate genus or species or with genomes of commensal strains within the candidate genus or species or with human genome sequence; identify a set of neighborhood genes present upstream and downstream of the identified set of nucleotide repeat sequences on the pathogen genome; annotate the identified set of neighborhood genes according to functional roles of each of the identified set of neighborhood genes in pathways in their respective antibiotic induced pathogens; test the presence of a secondary structure in the identified set of nucleotide repeat sequences, wherein the secondary structure is at least one of a palindromic or non-palindromic structure. The administration module prepares and administers a construct on the infected area depending on the presence of the secondary structure to treat the infections due to the antibiotic induced pathogens.

In another aspect, a method for combating infections due to antibiotic induced pathogens is provided. Initially, a sample is obtained from an infected area. Further, DNA is isolated from the obtained sample using one of a laboratory methods. Later, the isolated DNA is sequenced. In the next step. presence of the antibiotic induced pathogens is detected using a plurality of detection methods, wherein the antibiotic induced pathogens comprise one or more of *Clostridium difficile*, vancomycin-resistant *Enterococcus faecalis* and vancomycin-resistant *Enterococcus faecium* from the isolated DNA of the sample. Further, an engineered polynucleotide construct is prepared and administered on the infected area to combat the infections due to the antibiotic induced pathogens, wherein the engineered polynucleotide construct is comprising: one or more of a set of nucleotide repeat sequences with multiple copies at dispersed locations on the genomes of one or more of the *Clostridium difficile*, vancomycin-resistant *Enterococcus faecalis* and vancomycin-resistant *Enterococcus faecium* genomes, wherein the set of nucleotide repeat sequences comprises one or more of a Sequence ID 001, a Sequence ID 002, a Sequence ID 003, reverse complement of the Sequence ID 001, reverse complement of the Sequence ID 002 or reverse complement of the Sequence ID 003, a first enzyme capable of nicking and cleaving the identified set of nucleotide sequences, and a second enzyme capable of removal of a set of neighborhood genes flanking the set of nucleotide repeat sequences. At the next step, the efficacy of the administered engineered polynucleotide construct to combat the antibiotic induced pathogens is checked after a predefined time period. And finally, the engineered polynucleotide construct is re-administered if the antibiotic induced pathogens are still present in the infected area post administering.

The target sites or nucleotide repeat sequences in this disclosure refer to nucleotide sequences which repeat a minimum number of ten times within the genome of the candidate pathogen/pathogens which are identified in an infected site from which the sample is collected. These nucleotide repeat sequences can be targeted in order to debilitate the pathogen. The mentioned nucleotide repeat sequence/sequences is selected if it occurs more than 10 times in all the strains of the candidate specie or genus to which the candidate pathogen/pathogens identified in an infected site belong. The nucleotide repeat sequence is selected such that it does not occur more than twice in genomes of strains belonging to any other genus than that of the candidate pathogen and does not occur more than twice within the genome of the host.

In yet another aspect, one or more non-transitory machine readable information storage mediums comprising one or more instructions which when executed by one or more hardware processors cause combating infections due to antibiotic induced pathogens is provided. Initially, a sample is obtained from an infected area. Further, DNA is isolated from the obtained sample using one of a laboratory methods. Later, the isolated DNA is sequenced. In the next step. presence of the antibiotic induced pathogens is detected using a plurality of detection methods, wherein the antibiotic induced pathogens comprise one or more of *Clostridium difficile*, vancomycin-resistant *Enterococcus faecalis* and vancomycin-resistant *Enterococcus faecium* from the isolated DNA of the sample. Further, an engineered polynucleotide construct is prepared and administered on the infected area to combat the infections due to the antibiotic induced pathogens, wherein the engineered polynucleotide construct is comprising: one or more of a set of nucleotide repeat sequences with multiple copies at dispersed locations on the genomes of one or more of the *Clostridium difficile*, vancomycin-resistant *Enterococcus faecalis* and vancomycin-resistant *Enterococcus faecium* genomes, wherein the set of nucleotide repeat sequences comprises one or more of a Sequence ID 001, a Sequence ID 002, a Sequence ID 003, reverse complement of the Sequence ID 001, reverse complement of the Sequence ID 002 or reverse complement of the Sequence ID 003, a first enzyme capable of nicking and cleaving the identified set of nucleotide sequences, and a second enzyme capable of removal of a set of neighborhood genes flanking the set of nucleotide repeat sequences. At the next step, the efficacy of the administered engineered polynucleotide construct to combat the antibiotic induced pathogens is checked after a predefined time period. And finally, the engineered polynucleotide construct is re-administered if the antibiotic induced pathogens are still present in the infected area post administering.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles:

FIG. 2 shows nucleotide repeat sequences along with neighborhood genes in the *Clostridium difficile* genome according to an embodiment of the disclosure.

FIG. 6 is a flowchart illustrating the steps involved in combating infections due to antibiotic induced pathogens according to an embodiment of the present disclosure.

DETAILED DESCRIPTION OF EMBODIMENTS

Figure 1:
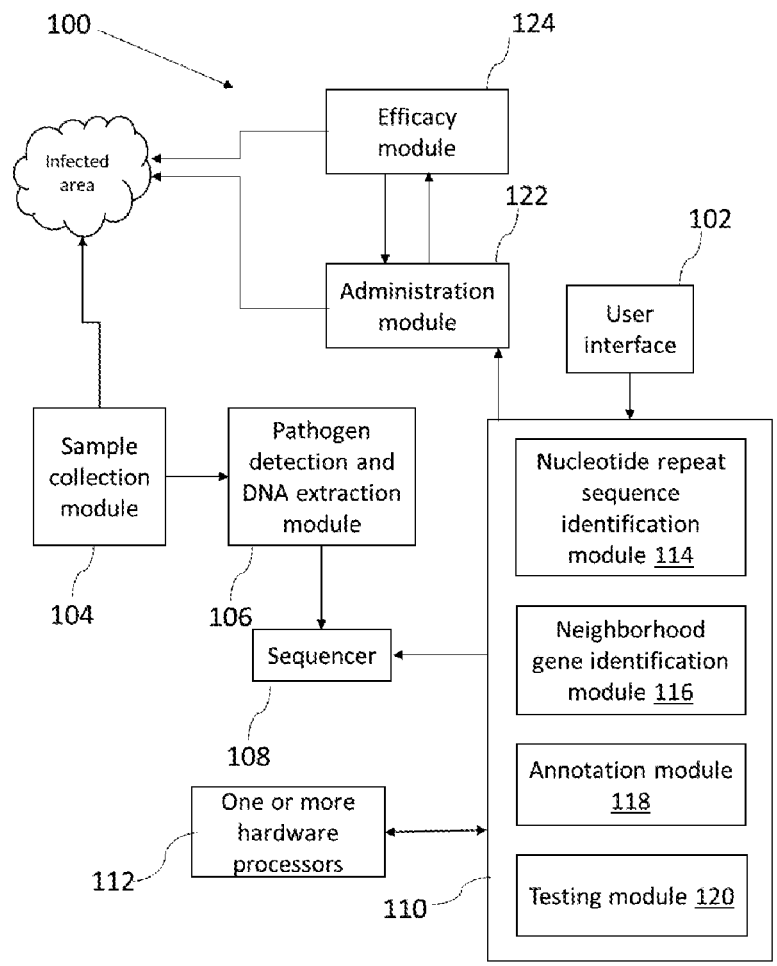
FIG. 1 illustrates a block diagram of a system for combating infections due to antibiotic induced pathogens according to an embodiment of the present disclosure.
Figure 3:
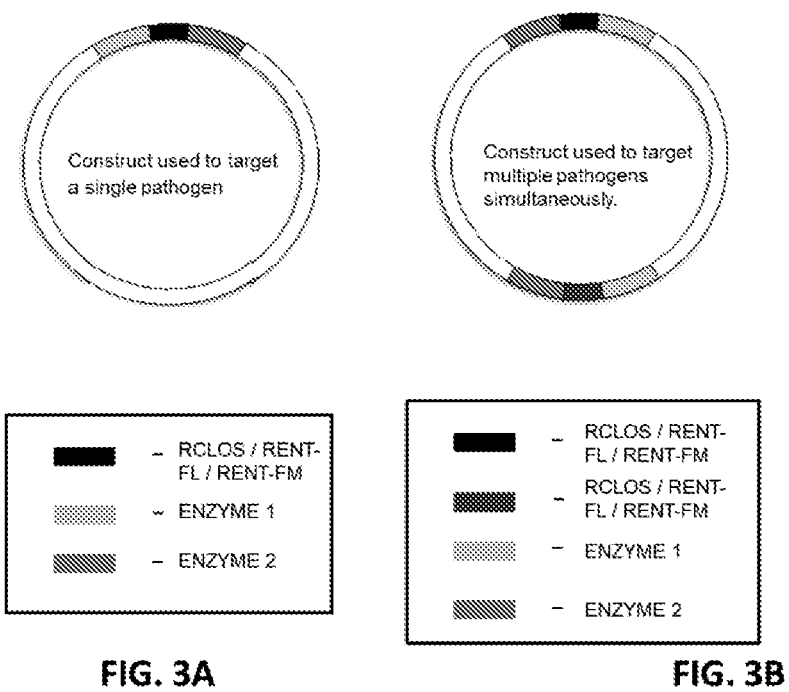
FIGS. 3A and 3B show components of a construct containing multiple target sequences capable of combating single and multiple antibiotic induced pathogenic infection respectively according to an embodiment of the disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Glossary—Terms Used in the Embodiments with Explanation

The expression "nucleotide repeat sequence" or "repeated nucleotide sequences" or "repeat sequence" or "the set of nucleotide repeats" or "repeated sequence regions" or "similar sequence stretches" or "target sequence" or "target sites" or "target nucleotide repeat sequence" or "conserved stretch of nucleotide sequences" or "repeat element" in the context of the present disclosure refers to nucleotide sequences which have been repeated multiple times in a sequence of DNA extracted from a sample obtained from the infected area or within nucleotide sequence obtained for a genomic sequence of a pathogen or genomic sequences of strains belonging to a pathogenic genus or specie.

The term "metagenome refers" to the genetic material derived directly from the infected site and can be considered representative of overall microorganisms present in a sample collected from an environment. The information about metagenome and its taxonomic constitution is obtained by either sequencing the genes considered as markers for different taxa (for example, 16S rRNA), amplifying genes of interest using specific primers through methods like but not limited to Polymerase Chain Reaction (PCR). This information can also be obtained by whole genome sequencing of the obtained environmental or metagenomic sample. The sample collected from the environment is referred to from now on as metagenomic sample.

The term "identified nucleotide repeat sequence is dispersed across distant locations in the pathogen genome" or "dispersed location" refers to the fact that the nucleotide sequences identified in this method are spread at distant locations across the pathogen genome.

In this disclosure, the terms "distant location" or "distinct location" or "dispersed location" refer to locations of two nucleotide repeat sequences that are separated by >10000 base pairs. Nucleotide repeat regions having distance less than 10000 base pairs between their locations have been considered as clustered repeats.

The expression "candidate genus" or "candidate pathogen" refers to the genus, specie or pathogen in which the nucleotide repeat sequence is identified and is used as a target sequence/site.

The term "commensal" refers to microbe/microbes which are considered beneficial to the host or cause no harm to the host.

The term 'pathogen' refers to microbe/microbes which cause a disease in host.

The term 'host' refers to either a living organism or an environmental site. In an embodiment, 'host' may refer to human, animal or plant in which a pathogenic infection may be observed.

The term 'non-culturable' refers to microbes that cannot be grown in laboratory settings because the ideal conditions and media for their growth is not well characterized. Such microbes can be analyzed by culture independent methods discussed in various embodiments of the disclosure.

Referring now to the drawings, and more particularly to FIG. 1 through FIG. 7, where similar reference characters denote corresponding features consistently throughout the figures, there are shown preferred embodiments and these embodiments are described in the context of the following exemplary system and/or method. According to an embodiment of the disclosure, a system 100 for combating infections due to antibiotic induced pathogens is shown in the block diagram of FIG. 1. The system 100 is configured to provide strategies to combat pathogenic infections caused by multi-drug resistant (MDR) and extensively drug resistant (XDR) strains of antibiotic induced pathogens. The strategy involves identifying potential target sites which occur at distant locations in multiple copies in a pathogen genome and which can be utilized to compromise pathogen's multiple virulence or essential functions at the same time.

The system is configured to provide strategies to combat pathogenic infections caused by multi-drug resistant (MDR) and extensively drug resistant (XDR) strains of antibiotic induced pathogens. The idea used in this disclosure utilizes the fact that multiple occurrences of a conserved stretch of nucleotide sequence on a pathogen genome and surrounded by genes encoding virulence factors or which are in vicinity of genes essential for survival of the candidate pathogen can be targeted to disrupt the overall genetic machinery of the pathogen. In the present disclosure genomic neighborhood or vicinity or 'flanking genes' refers to regions lying within a predefined number of genes to the identified conserved stretch of nucleotide sequence (or its reverse complement) on the candidate pathogen genome or within a distance of predefined number of bases with respect to the conserved stretch of nucleotide sequence (or its reverse complement) on the genome of the pathogen genome. In an embodiment the genomic neighborhood or flanking genes may comprise of 10 genes lying on either side of identified conserved stretch of nucleotide sequence or its reverse complement in terms of its location on the pathogen genome. The important functional genes in this disclosure refer to the genes in pathogens which encode for proteins which are critical for survival, pathogenicity, interaction with the host, adherence to the host or for the virulence of pathogen. In an embodiment the genomic neighborhood or flanking genes may comprise of 10 genes lying on either side of conserved stretch of nucleotide sequence or its reverse complement in terms of its location on the pathogen genome.

These conserved stretch of nucleotide sequences might also lie in the neighborhood of genes which perform other critical functions in a pathogen. A conserved stretch of sequence refers to a nucleotide repeat sequence which occurs within all pathogenic genomes belonging to a candidate genus. Another important factor would be occurrence of these nucleotide repeat sequences on the genomes of only the genomic sequences of pathogenic strains of the candidate pathogens and having minimum cross reactivity with the commensals (belonging to same candidate genus or other genera) as well as with the host itself. Cross reactivity, in this disclosure, refers to the occurrence of these conserved stretches of nucleotide repeat sequences more than twice in the host genome or in genomes of genera/species other than the candidate genus/specie or more than twice within genomes of commensal bacteria belonging to the candidate genus/species for which this sequence is being utilized as a target. Further, the identified potential target sites in pathogen are not specific to a single strain of the pathogen. In most cases, metagenomic samples contain bacteria whose strain level information cannot be obtained. Thus, the method can be utilized to target all strains of pathogens in the given candidate genus/species of the bacteria and is not hindered by the absence of strain level information.

The present disclosure has been specifically explained on the sequenced genomes of *Clostridium difficile* and vancomycin-resistant *Enterococcus* sp. *Clostridium difficile* is associated with antibiotic induced diarrhea in hospitalized or recently hospitalized patients. Vancomycin-resistant *Enterococcus* sp. comprises vancomycin-resistant *Enterococcus faecalis* and vancomycin-resistant *Enterococcus faecium*. As the name suggests they are resistant to antibiotic vancomycin which is used as a last resort treatment method.

According to an embodiment of the disclosure, the system 100 consists of a user interface 102, a sample collection module 104, a pathogen detection and DNA extraction module 106, a sequencer 108, a memory 110 and a processor 112 as shown in FIG. 1. The processor 112 is in communication with the memory 110. The memory 110 further includes a plurality of modules for performing various functions. The memory 110 may include a nucleotide repeat sequence identification module 114, a neighborhood gene identification module 116, an annotation module 118 and a testing module 120. The system 100 further comprises an administration module 122 and an efficacy module 124 as shown in the block diagram of FIG. 1.

According to an embodiment of the disclosure, the sample is collected from the infected area using the sample collection module 104. In this module, the method utilized for extracting samples from the infected sites depends largely on the site of infection. In an embodiment where site of infection is the gut (for example infection caused by *Clostridium difficile*), fecal/stool samples may be collected to identify the pathogen infecting the gut. The collected samples from the infected area is one or more of fecal matter, blood, urine, tissue biopsy, hospital surfaces or environmental samples. Samples may be collected using endoscopic biopsy of gastrointestinal tract. In another embodiment, in case of blood borne pathogens such as vancomycin-Resistant *Enterococcus* sp. (in case of chronic infection of VRE) the sample is extracted through collection of blood components. Acute serum collected from the patients (containing high concentration of infectious bacteria) can be used. Additionally, the whole blood sample can be submitted for bacterial culturing or the whole blood plasma can be utilized for further procedure.

In another embodiment the site of infection can also be an environment such as soil, air, water or surfaces etc. Sample collection from a surface can be performed using a sterile swabs. Dry swabs may be recommended for wet surfaces and wet swabs may be recommended for dry surfaces. Swabbing of the test surface may be performed by rolling the swab lightly back and forth. Water and soil samples can be collected from the environmental site of infection and sent for further procedure. Air samples can also be collected to identify the presence of air borne pathogens. Volumetric air samples for culture analyses can be taken by impacting a known volume of air onto a suitable growth medium. Any other laboratory accepted method of sample extraction/collection from environment as well as living organisms is within the scope of this invention.

DNA/RNA is isolated and then extracted from the sample using laboratory standardized protocol using the DNA extraction module 106 and sequencing is performed using the sequencer 108. The nucleotide sequences obtained after sequencing of extracted DNA/RNA sequences are then provided to the processor 112 using the user interface 102. The nucleotide sequences can be obtained for 16S rRNA, or a nucleotide sequence encoding for any particular gene of interest being amplified, or sequences of DNA fragments corresponding to whole genome sequencing or shotgun sequencing. In one embodiment, DNA/RNA can be extracted using miniprep isolation kits and other methods standardized in laboratory setups. The sequences obtained are fed into the processor 112. The user interface 102 is operated by an user. The user interface 102 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

The pathogen detection and DNA extraction module 106 is also configured to utilize experimental techniques to detect pathogens present in an infected site. The use of any laboratory acceptable methods of detecting presence of pathogens present at the infected site is within scope of the disclosure. In one embodiment, presence of viable living cells can be detected by utilizing presence of bacterial mRNA which has a short half-life and will not exist once the cells are dead. This mRNA based method may involve identifying antigen/protein specific for the pathogen which can be utilized as a marker for that pathogen and produced by the pathogen in abundance and the corresponding gene on the pathogen genome can be obtained (for e.g. Toxins A and B of *Clostridium difficile* and Enterocins in VRE, etc.). The mRNA corresponding to expression of these genes can be detected using techniques like but not limited to reverse transcriptase polymerase chain reaction (RT-PCR) assays or reverse transcriptase strand displacement amplification (RT-SDA) assays. In another embodiment, expression of proteins identified as specific to these pathogens can be detected using various laboratory accepted methods for protein purification and detection (for e.g. toxins A and B in *Clostridium difficile* and Enterocins in VRE, etc.). Chromogenic enzyme assays for a pathogen are also within scope of the invention. Specific metabolites or compounds produced by a pathogen can also be detected (using different laboratory acceptable methods like Mass spectrometry, HPLC-MS, spectrometry-based methods, etc.) to ascertain pathogen presence (e.g. Toxins A and B in *Clostridium difficile* and Enterocins in VRE, etc.). In other embodiments, methods like nucleic acid amplification tests (NAAT), real time PCR, immunoassays for the identified antigens as well as specific staining and microscopy techniques and flow cytometry methods of detecting pathogens are also within scope of this invention. PCR or Restriction Fragment Length Polymorphism (RFLP) based detection of 16S rRNA in order to identify pathogens can also be utilized. In one more embodiment, staining methods can also be utilized to identify a pathogen and establish viability of a pathogen cell (e.g. propidium iodide can be used for identifying dead cells). Cell toxicity assays can also be utilized for toxins (e.g Toxins A and B of *Clostridium difficile* and Enterocins in VRE) based detection of pathogens. Further in case of sporulating bacteria, spore detection assays can also be utilized. In case of culturable bacteria, the viability of pathogens can even be established using culturing methods using selective media followed by methods to detect specific pathogens discussed above. In case of an infection in living beings, observation of phenotypic effects like alleviation of infection symptoms is also within scope of this disclosure. The symptoms may vary with type of infection and may be observed by registered medical practitioner or healthcare professional. Any other method of detecting pathogens are also within scope of this disclosure.

According to an embodiment of the disclosure, the DNA extraction module 106 is configured to applying one or more techniques for identification or detection of microbes in a collected sample comprising a sequencing technique, a flow cytometry based methodology, a microscopic examination of the microbes in collected sample, microbial culture of pathogens in vitro, immunoassays, cell toxicity assay, enzymatic, colorimetric or fluorescence assays, assays involving spectroscopic/spectrometric/chromatographic identification and screening of signals from complex microbial populations, The pathogen or microbial characterization data may comprise one or more of sequenced microbial DNA data, a Microscopic imaging data, a Flow cytometry cellular measurement data, a colony count and cellular phenotypic data of microbes grown in in-vitro cultures, immunological data, proteomic/metabolomics data, and a signal intensity data. The sequenced microbial data obtained from sequencer 108 comprises sequences obtained from next generation sequencing platforms comprising one or more of corresponding to marker genes including 16S rRNA, Whole Genome Shotgun (WGS) sequencing, a fragment library based sequences, a mate-pair library or a paired-end library based sequences, or a combination thereof. The sequencing data may also comprise of complete genome sequences of the pathogens obtained within a collected sample. In one embodiment, the taxonomic groups or pathogens within a sample collected can be obtained by amplification of marker genes like 16S rRNA within bacteria. In another embodiment, the taxonomic groups or pathogens within a sample can be obtained by the binning of whole genome sequencing reads into various taxonomic groups using different methods including sequence similarities as well as several methods using supervised and unsupervised classifiers for taxonomic binning of metagenomics sequences.

According to an embodiment of the disclosure, the processor 112 comprises the nucleotide repeat sequence identification module 114. The nucleotide repeat sequence identification module 114 is configured to identify a set of nucleotide repeat sequences in the extracted DNA which occur more than a predefined number of times refers to as the number of occurrences of nucleotide repeat sequence on genomic sequences of all pathogenic strains of candidate pathogens in a dispersed manner and this number might vary with system and pathogen under consideration. A minimum of 10 occurrences dispersed at distant locations on the genome of the pathogen is required for a nucleotide repeat sequence to be considered. In an example, RCLOS/RENT-FL/RENT-FM is identified as the nucleotide repeat sequence in *Clostridium difficile*/VRE genome as shown in schematic representation of FIG. 2. Further, it is important to ensure that the identified nucleotide repeat sequence region is specifically present on the genomes of a particular candidate pathogenic genus only and, nucleotide sequence based alignment of this region does not show more than two cross matches with commensals belonging to genera other than candidate pathogenic genus or with any commensals within same candidate pathogenic genus. In addition to that, the identified set of nucleotide repeat sequences are not specific to a single strain of the pathogen. The antibiotic induced pathogens comprise one or more strains of pathogens whose occurrence can be induced by intake of antibiotics specifically pertaining to *Clostridium difficile*, vancomycin-resistant *Enterococcus faecalis* and vancomycin-resistant *Enterococcus faecium*. For example, nucleotide repeat sequences RCLOS is present in all sequenced strains of *Clostridium difficile*, RENT-FL is present in the multiple strains of vancomycin-resistant *Enterococcus faecalis* and RENT-FM is present in multiple pathogenic strains of vancomycin-resistant *Enterococcus faecium*. In most cases, metagenomic samples contain bacteria whose strain level information cannot be obtained. Thus, the method can be utilized to target all pathogens in the given species of the bacteria and is not hindered by the absence of strain level information and making it more robust.

Following method can be used for the identification of the nucleotide repeat sequence region on a genome. Conserved nucleotide repeat elements were identified on *Clostridium difficile*, vancomycin-resistant *Enterococcus faecalis* and vancomycin-resistant *Enterococcus faecium* genomes by taking nucleotide sequence stretches of predefined length Rn (30-60 in this embodiment in all three cases) picked from the genome sequence of candidate pathogen or different strains of candidate pathogen, keeping the difference in the start position of two consecutive picked nucleotide sequence stretches $Rn_{i+1}$ and $Rn_i$ as 5 nucleotides. Predefined length Rn refers to the length of a stretch of nucleotide sequence (picked from the complete nucleotide sequence of a bacterial genome) used as a seed input for local sequence alignment tools to be aligned to the candidate genome it has been obtained from. In the next step, a reference genome based nucleotide sequence alignment tool is applied in order to align the picked nucleotide sequence stretch with nucleotide sequences corresponding to genomes of all pathogenic strains belonging to the candidate pathogen, genus or specie. This procedure identifies the nucleotide sequence stretches which occur multiple times and on distant locations on the bacterial genomes (nucleotide repeat sequences). This predefined length may differ depending on the pathogen. In this implementation, stretches of sequences were aligned within the genome by local alignment (as implemented in PILER software) to find the location of RCLOS, RENT-FL and RENT-FM in all sequenced *Clostridium difficile*, vancomycin-resistant *Enterococcus faecalis* and vancomycin-resistant *Enterococcus faecium* genomes respectively. Sequence based search utilizing any other sequence alignment or repeat finding tools are within scope of this invention. Nucleotide repeat sequences $R_n$ occurring more than 15 times at distant locations on the genome were considered. If the number of times $R_n$ matches on the genomic sequences of strains of candidate pathogen genome/genomes is greater than the predefined threshold with a minimum value of 10, the nucleotide sequence stretch is termed as target nucleotide repeat sequence. This number of occurrences may vary depending on the system requirements but a minimum occurrence of 10 times on a pathogen sequence is required for a nucleotide sequence to be considered as a target sequence. The nucleotide repeat sequences which are conserved across all genome sequences corresponding to strains of a candidate pathogen or genus would indicate the said conserved sites. Any other method of identification of conserved sites is also within the scope of this disclosure.

According to an embodiment of the disclosure, the processor 112 further includes the neighborhood gene identification module 116. The neighborhood gene identification module 116 is configured to identify a set of neighborhood genes present upstream and downstream of the set of nucleotide repeat sequences on the genome sequence of antibiotic induced pathogens. In the present embodiment, on each genome where nucleotide repeat elements occur, 10 flanking genes both upstream and downstream were found on each strand (+ and −) of DNA. The number of flanking genes considered may vary with the system. In the example of the present embodiment, on each *Clostridium difficile*, vancomycin-resistant *Enterococcus faecalis* and vancomycin-resistant *Enterococcus faecium* genomes where nucleotide repeat elements RCLOS, RENT-FL and RENT-FM occur respectively, 10 flanking genes on both upstream and downstream of the genomes of these pathogens were found on each strand (+10 and −10) of DNA of these pathogens.

According to an embodiment of the disclosure, the system 100 further includes the annotation module 118. The annotation module 118 categorizes or annotates the set of neighborhood genes on the pathogen genomes based on their functional roles in the pathogen. Functional annotation of these genes was performed using HMM search with PFAM as the database. In other embodiments, databases like CDD, SMART etc. can be utilized. The use of any other methods such as PSSM, BLAST etc. is well within the scope of the disclosure.

These dispersed nucleotide repeat sequences at distant locations on the pathogen genome can be used as targets which can be further extended to target multiple flanking genes (which includes virulence and survival genes) on the pathogen genome simultaneously at distant multiple locations and carry out changes like but not limited to gene silencing, gene recombination, gene substitution with a new function etc.

Functional categorization based on pathways of these genes flanking the identified pathogen targets nucleotide repeats RCLOS, RENT-FL and RENT-FM on the pathogen genome are involved in was carried out using literature mining. The broad categories have been discussed in Table 1, Table II and Table III.

TABLE 1

Summary of proteins in vicinity conserved sequence RCLOS repeated in *Clostridium difficile* genome

| Category | Genes | Function |
|---|---|---|
| Pathogenic/Virulence Proteins | | |
| Toxins | Toxin A | *Clostridium difficile* Toxin A is enterotoxin |
| | Toxin B | *Clostridium difficile* toxin B is a cytotoxin |
| | RelA-spoT | Involved in synthesis of ppGpp molecule that enhances further virulence |
| Survival proteins | | |
| Antibiotic resistance | Beta - lactamases | Involved in cleaving the lactum ring in antibiotics thereby making them inert |
| DNA Repair machinery | MutS | Mismatch repair protein |
| | DNA exonucleases | Cleaves DNA fragments at the end |
| | DNA methyltransferase | Involved in methylation of DNA bases |
| Stress Response | CSP - Carbon starvation protein | Produced under starvation condition |
| | TerD - tellurium resistance protein | Produced in response to influx of toxic tellurium ions |
| | Cold shock protein | Produced in response to drastic temperature changes |
| | TelA (anion resistance) | Produced in response to toxic anionic compounds |
| | Radical SAM domain containing protein | Produced in response to oxidative stress due to ROS |
| Essential Proteins | | |
| Essential Proteins | Metabolism of essential metabolites | Glycogen metabolism, threonine, lysine, histidine metabolism, folate metabolism, formate metabolism, succinyl-CoA formation etc |
| | Cell Wall Biosynthesis (N-acetylmuramoyl-L-alanine amidase, D-alanyl-D-alanine carboxypeptidase) | Proteins essential to the formation of bacterial peptidoglycan layer |
| | Signal transduction | Transcriptional regulators (LysR,TetR), transcriptional anti-terminators etc |
| | Transporters | ABC transporter and PTS system specific transporter |

TABLE 2

Summary of proteins in vicinity of conserved sequence RENT-FL repeated in *Enterococcus faecalis* genome

| Category | Genes | Function |
|---|---|---|
| Pathogenic/Virulence proteins | | |
| Toxins | Staphylococcal toxin | Causes toxic shock syndrome leading to vomiting and diarrhea |
| Host Immune Response | Sortase | Protein responsible for attaching various antigens to bacterial cell surfaces |
| Survival proteins | | |
| Antibiotic resistance | Beta lactamase | Involved in cleaving the lactum ring in antibiotics thereby making them inert |
| Competence Protein | ComEC/ComEA/T2SF/T2SE | Regulates the uptake of extracellular DNA fragments |
| DNA repair machinery | Uvr_D | DNA excision repair helicase |
| | RexA/B exonuclease recombinase | DNA modification through homologous recombination |
| | RuvB | DNA junction binding helicase |
| | RadC | DNA repair protein |
| | Topoisomerase | Unwinds negative supercoiling in DNA |
| | ParB | DNA repair protein |
| | uracil-DNA glycosylase | Involved in excision repair mechanism |
| | DNA polymerase | Involved in DNA synthesis |
| Stress Response | Usp | Universal stress response |
| | Radical SAM domain containing protein | Produced in response to oxidative stress due to ROS |
| | Cold shock protein | Produced in response to drastic temperature changes |
| | Cell envelop associated phosphatase | Cell wall stress homeostasis and bacitracin resistance |
| Essential proteins | | |
| Essential Proteins | N-acetylmuramic acid 6-phosphate etherase, Murein ligase, D-alanine carboxypeptidase, Pectate lyase | Bacterial peptidoglycan layer formation and degradation (pectate lyase) |
| | purine catabolism, Pyrimidine biosynthesis, tRNA synthetase, inosine-5'-monophosphate dehydrogenase | Nucleic acid metabolism |
| | Phosphofructo kinase phosphate acetyltransferase | Glucose metabolism Involved in pyruvate metabolism |
| | cytochrome d ubiquinol oxidase subunits I/II | Involved in bacterial electron transport chain |
| | type 2 phosphatidic acid phosphatase | Key enzyme in lipid metabolism |
| | GidA/B | 16s rRNA methyltransferase |
| | MFS, PTS, ABS, Citrate, Cation transporters | Transport of essential components across membranes |
| | ArcC,GNTR | Transcriptional regulators (signal transduction) |

TABLE 3

Summary of proteins in vicinity of conserved sequence RENT-FM repeated in *Enterococcus faecium* genome

| Category | Genes | Function |
|---|---|---|
| *Pathogenic/Virulence Proteins* | | |
| Host Immune Response | myosin-cross-reactive antigen | Induces immune response in humans |
| | Isochorismatase | Is essential in inducing autophagy in human cells |
| *Survival Proteins* | | |
| DNA repair machinery | Uvr_D | DNA excision repair helicase |
| | DNA polymerase III | Involved in DNA synthesis |
| | Topoisomerase | Unwinds negative supercoiling in DNA |
| | MutS_V | DNA mismatch repair protein |
| | RecJ family exonuclease | Single-stranded DNA repair machinery |
| | RecU | Recombination protein involved in DNA repair |
| | RNase_T | Involved in DNA repair |
| | RecR | Recombination protein involved in DNA repair |
| Antibiotic resistance | Beta lactamase | Involved in cleaving the lactum ring in antibiotics thereby making them inert |
| | VanZ | Confers teicoplanin resistance |
| Stress Response | peptide methionine sulfoxide reductase | Repairs proteins under oxidative stress |
| | TelA | tellurite resistance protein |
| | Radical_SAM | ROS stress response |
| | Asp23 | Alkaline shock response protein |
| | CtsR | Repressor of class III response |
| | Usp | Universal Shock protein |
| | CSD | Cold Shock protein |
| | Enterocin A Immunity | Provides immunity against enterocin produced against other bacterial species |
| Competence Protein | CinA | competence/damage-inducible protein |
| *Essential Proteins* | | |
| Transport | PTS System | Extensively involved in bacterial sugar uptake |
| | Ferrous transport | Iron transport system |
| | ABC Transport | Involved in major transport of molecules |
| | MFS transport | Involved in major transport of molecules |
| Cell Wall Biosynthesis | Mur_ligase | Muramoyl ligase involved in bacterial cell wall synthesis |
| | Polysacc_synt | polysaccharide biosynthesis family protein |
| Transcription regulators | AraC, LysR, GnTR, LuxR | Various essential transcription regulators |
| DNA synthesis | tRNA_synt, IMPDH | Involved in tRNA synthesis and de novo DNA synthesis respectively |
| Metabolism | G6PD_C,G6PD_N; fructokinase, | Involved in various essential metabolism processes such as glycolysis etc |
| Cellular Function | Phospholipase D | Involved in various cellular functions such as cell division |

According to an embodiment of the disclosure, the system 100 further includes the testing module 120 and the administration module 122. The testing module 120 is configured to check the presence of secondary structure formation in the identified set of nucleotide repeat sequences. There could be the presence of the secondary structures such as hairpin loop formation. Depending on the presence of the secondary structure, the administration module 122 is configured to administer an engineered construct to treat the pathogenic infection. wherein the engineered polynucleotide construct is comprising: one or more of the first and the second set of nucleotide repeat sequences with multiple copies at dispersed locations on the candidate pathogen genomes of one or more of the antibiotic induced pathogens, wherein the first set of nucleotide repeat sequences comprises a Sequence ID 001 or reverse complement of the sequence ID 001, and the second set of nucleotide repeat sequences comprises one or more of a Sequence ID 002, a Sequence ID 003, reverse complement of the Sequence ID 002 or reverse complement of the Sequence ID 003, Sequence ID 004 or reverse complement of the Sequence ID 004 and Sequence ID 005 or reverse complement of the Sequence ID 005, a first enzyme capable of nicking and cleaving the identified set of nucleotide sequences, and a second enzyme capable of removal of a set of neighborhood genes flanking the set of nucleotide repeat sequences. The construct works in such a way that it targets multiple regions in the genome simultaneously.

In an embodiment the construct may comprise of an engineered circular DNA comprising of an origin of replication. Further the construct may comprise of regulatory elements including a promoter sequence, ribosomal binding site, start codon, a cassette comprising of first and second enzyme flanking the identified nucleotide repeat sequence or the reverse complement (antisense) of one or more of the nucleotide repeat sequence RCLOS/RENT-FL/RENT-FM cloned into the system, stop codons and transcription terminator. The construct may also be equipped to create a poly A tail in mRNA to stabilize the sequence. The poly A tail refers to a stretch of polynucleotide Adenine nucleotides at the 3' end of mRNA. The promoter sequence may depend on the pathogen being targeted as well as the regulation required to express the components of the construct at a specific targeted site (for example, within a living being or an infected area). In one embodiment, the first and second enzyme can be nickase and exonuclease/endonuclease cloned in any order. The target RCLOS/RENT-FL/RENT-FM within the pathogen genome can be recognized and bound by the reverse complement sequence of these nucleotide repeat sequence RCLOS/RENT-FL/RENT-FM and the complex thus formed can be nicked by the nickase enzyme. Any other enzymes capable of creating nicks on the bound target sequence as well as cutting the flanking regions of DNA starting from the nicks is within scope of this invention. The nicked part may comprise of blunt ends or sticky ends depending on the enzyme used for creating nicks. The exonuclease can then cut the duplex as well as flanking genes once it recognizes a nick. In another embodiment, in addition to the above mentioned features, if bacterial conjugation is to be used as a construct delivery method, the construct may comprise of a relaxase, coding sequences for structural proteins (e.g., pili) and those for regulatory proteins for conjugation. These polynucleotides comprising the identified nucleotide repeat sequence, the genes encoding enzymes and the other features discussed above can be inserted into laboratory acceptable vectors which allow insertion of external DNA fragments. In one embodiment construct may be carried by vectors like plasmid or phage based cloning vectors. The regulatory elements can be designed according to information available for the pathogen being targeted.

In another embodiment, the enzymes can be cas9 sequences (may be obtained from *Streptococcus pyogenes*) flanking the forward or reverse complement of nucleotide repeat sequence RCLOS/RENT-FL/RENT-FM which can act as sgRNA (single guide RNA) for the obtained CRISPR-Cas (Clustered Regularly Interspaced Short Palindromic Repeats) system. The reverse complement of target nucleotide repeat sequence is obtained by interchanging letters A and T and interchanging letters C and G between target and complement sequences. The reverse complement refers to the sequence corresponding to the identified nucleotide repeat sequence in the opposite strand of DNA. The target nucleotide repeat sequence RCLOS/RENT-FL/RENT-FM or its reverse complement is recognized by the reverse complement sequence or target complement sequence respectively on the construct and the complex is formed. The cas9 may then act as an endonuclease and cut the nick and flanking sequences. The target nucleotide repeat sequence can be targeted by delivering an engineered polynucleotide construct using a bacterial, plasmid or a viral vector to the target bacterial cell. In one embodiment the composition of the construct may comprise of the first element comprising a polynucleotide sequence of CRISPR-Cas system wherein the polynucleotide sequence may comprise a nucleotide sequence called a guide sequence capable of hybridizing to target sequence in pathogen, a tracr sequence and a tracr mate sequence. The second element may comprise of CRISPR enzyme coding sequences like CAS enzymes. It should be noted that in all these embodiments multiple nucleotide repeat sequences RCLOS/RENT-FL/RENT-FM can be cloned within same polynucleotide sequence along with a bacterial or viral vector and the other features mentioned above to target more than one pathogen using the same compact construct. Any other construct cassette that may bring about the recognition of the nucleotide repeat sequence RCLOS/RENT-FL/RENT-FM and subsequent cutting of nucleotide repeat sequence RCLOS/RENT-FL/RENT-FM and their flanking genes is within the scope of this invention.

In one embodiment, the construct may contain an enzyme 1, enzyme 2, identified target nucleotide repeat sequence, nucleotide repeat element (RCLOS/RENT-FL/RENT-FM) as shown in FIG. 3A. One of the enzyme 1 or enzyme 2 can be the nicking enzyme while the other will constitute nucleotide cleaving enzymes such as nuclease, exo-nuclease etc. Other enzymes with similar activities are also within scope of the invention. In another embodiment, the construct may be used to target multiple pathogens simultaneously as shown in FIG. 3B. The construct may contain nucleotide repeat element 1 as RCLOS/RENT-FL/RENT-FM and nucleotide repeat element 2RCLOS/RENT-FL/RENT-FM along with enzyme 1 and enzyme 2. One of the enzyme 1 or enzyme 2 can be the nicking enzyme while the other will constitute nucleotide cleaving enzymes such as nuclease, exo-nuclease etc.

Depending on the result of testing module 120, there could be two cases as follows:

Case I: If the identified nucleotide repeat sequences are found to be palindromic the following three strategies may be used.

Figure 4:
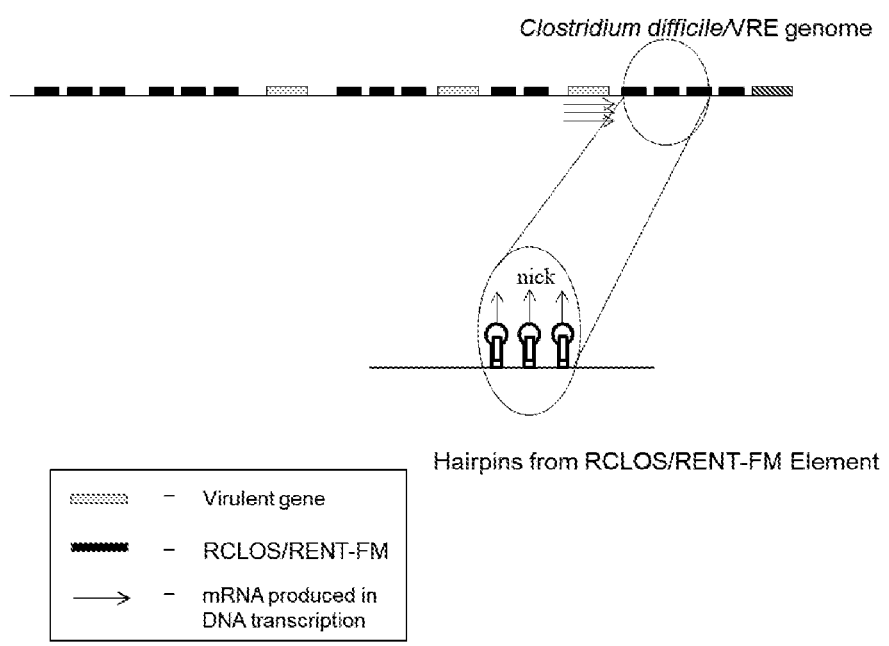
FIG. 4 shows targeting of palindromic and non-palindromic nucleotide repeat sequences in genomes of antibiotic induced pathogens according to an embodiment of the disclosure.

Strategy I includes handling hairpin loops which hinders DNA transcription by stalling the RNA polymerase enzyme thereby down-regulating the expression of flanking genes. In an embodiment, the strategy would involve use of the identified nucleotide repeat sequences as target and inserting a strong palindromic sequence to ensure the down-regulation of transcription of flanking genes Strategy II involves handling hairpin loops formed in the mRNA which could be involved in prevention of the early decay of mRNA thereby promoting the expression of important bacterial genes. In an embodiment, the strategy may include use of the identified nucleotide repeat sequences as target to nick the pathogen genome at multiple locations and cleave the flanking genes. In an example, a schematic representation of the *Clostridium difficile*/VRE genome showing nick of hairpins formed by RCLOS/RENT-FM element is shown in FIG. 4.

Strategy III is utilized if the identified nucleotide repeat sequences is found to be a transcription terminator and is followed by a polyA tail. In an embodiment, the identified nucleotide repeat sequence is used as target and a strong palindromic sequence is inserted to ensure that the transcriptional termination of the flanking genes occur and these genes are down-regulated in the pathogen.

Figure 5:
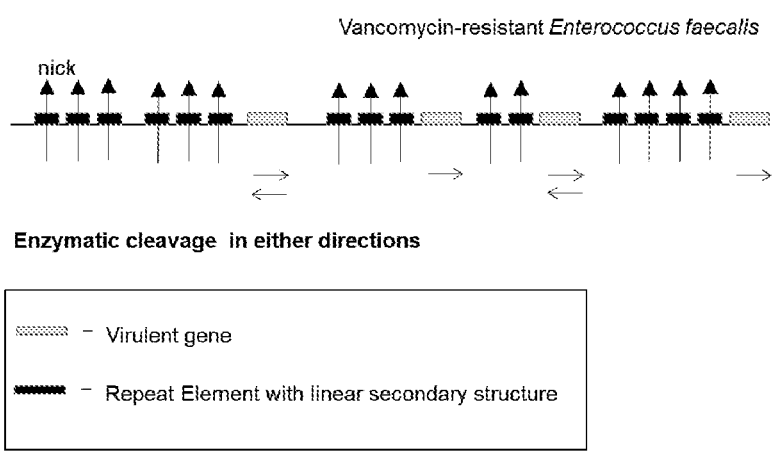
FIG. 5 shows enzymatic cleavage in the vancomycin-resistant *Enterococcus faecalis* genome according to an embodiment of the disclosure.

Case II: If the identified nucleotide repeat sequences are not found to be palindromic, the identified nucleotide repeat sequences are used as target to nick the pathogen genome at multiple locations and cleave the flanking genes. A schematic representation of vancomycin-resistant *Enterococcus faecalis* genome showing enzymatic cleavage in either directions is shown in FIG. 5.

In the present embodiment, the nucleotide repeat element RCLOS, RENT-FL and RENT-FM, which are used as example, only RCLOS and RENT-FM are palindromic and do form a hairpin loop structure indicating their role in regulation of transcription. These loops may either form at DNA level or at the ends of their mRNA during DNA transcription. This hairpin loop in the mRNA could be involved in prevention of the early decay of mRNA, resulting in higher protein formation of the virulence genes which are in the vicinity of these palindromic elements. Reduction in pathogenicity can be achieved by decreasing the stability of mRNA corresponding to these virulent genes which can be attained by removing the hairpin loops. If hairpin loop formation takes place at DNA level it might regulate DNA supercoiling.

For RENT-FL sequence which is non-palindromic, the identified nucleotide repeat sequences are used as target to nick the pathogen genome at multiple locations and cleave the flanking genes The administration module 122 can use any pharmaceutically acceptable method of carrying the construct to target the conserved sequences in a pathogen genome. In different embodiments the utility can be, but not limited to oral medicine, topical creams, nasal administration, aerosol sprays, injectable cocktail etc.

In an embodiment, the construct can be administered to the infected site (either living beings or environmental site) through targeted construct delivery methods such as the use of targeted liposomes wherein, the liposome is tagged on the external surface with molecules that may be specific and functionally important to the candidate genus and the tagged liposome can be used to transfer the construct into the pathogen, targeted nanoparticles wherein, a targeting molecule that is specific to the candidate genus can be attached to the nanoparticle (like but not limited to Ag or Au nanoparticle) along with the construct, thereby allowing the tagged nanoparticle to release the construct into the pathogen, phage based delivery method (wherein, the construct can be placed within the phage infecting the candidate genus thereby transferring the construct into pathogen) and bacterial conjugation (wherein, the construct can be placed in other bacteria that can conjugate with the candidate genus and the construct can be transferred to the pathogen through natural conjugation method), etc. In an embodiment, the lipid constitution of the membrane for the targeted liposome can be modified to target specific set of bacteria. In another embodiment, immunoliposomes can be created with specific antibodies towards ligands of specific pathogen (for example, antibodies against concanavalin A for targeting extracellular matrix of biofilms). The lipid bilayer can be made sensitive to the toxins or other virulence factors of the pathogen in order to release the construct only in infected areas where toxins are present. In another embodiment, the construct can be adsorbed or covalently linked to heavy metals (called gene guns or micro-projectiles) and carried to targeted pathogen bacterial cell.

In another embodiment, the construct can also be administered to the infected site through non-targeted construct delivery methods such as the use of non-targeted nanoparticles (wherein, nanoparticles can form cages that can hold the construct which are then released into the pathogen), non-targeted liposomes (wherein, the liposomes are phospholipid capsules which can be used to hold the construct that can then merge with the pathogen cell membrane to release the construct inside the pathogen) etc. In an embodiment, attenuated bacteria can also be used to deliver nanoparticles into tissue spaces where they can be released to act upon actual site of infection (as shown in creation of NanoBEADS in a study where *Salmonella* was used to deliver nanoparticles containing a drug to deep tissues). In another example, minicells produced by bacteria can also be used to package the construct and deliver it to specific areas in the infected site. In another embodiment, these delivery methods can be used to target the construct to infected surfaces also. Any other laboratory accepted method of administration of the construct to the infected site is within the scope of this disclosure.

According to an embodiment of the disclosure, the efficacy module 124 is used to assess the efficacy of the treatment methodology described in this disclosure. The efficacy module 124 comprises of any laboratory acceptable methods of detecting presence of pathogens present at the infected site. In one embodiment, presence of viable living cells can be detected by utilizing presence of bacterial mRNA which has a short half-life and will not exist once the cells are dead. This mRNA based method may involve identifying antigen/protein specific for the pathogen which can be utilized as a marker for that pathogen and produced by the pathogen in abundance and the corresponding gene on the pathogen genome can be obtained (for example, Toxins A and B in *Clostridium difficile* and Enterocin in VRE, etc.). The mRNA corresponding to expression of these genes can be detected using techniques like but not limited to polymerase chain reaction (RT-PCR) assays or reverse transcriptase strand displacement amplification (RT-SDA) assays. In another embodiment, expression of proteins identified as specific to these pathogens can be detected using various laboratory accepted methods for protein purification and detection (e.g. Toxins A and B in *Clostridium difficile* and Enterocin in VRE, etc.). Chromogenic enzyme assays for a pathogen are also within scope of the invention. Specific metabolites or compounds produced by a pathogen can also be detected (using different laboratory acceptable methods like Mass spectrometry, HPLC-MS, spectrometry-based methods, etc.) to ascertain pathogen presence (e.g. Toxins A and B in *Clostridium difficile* and Enterocin in VRE, etc.). In other embodiments, methods like nucleic acid amplification tests (NAAT), real time PCR, immunoassays for the identified antigens as well as specific staining and microscopy techniques and flow cytometry methods of detecting pathogens are also within scope of this invention. PCR or Restriction Fragment Length Polymorphism (RFLP) based detection of 16S rRNA in order to identify pathogens can also be utilized. In one more embodiment, staining methods can also be utilized to identify a pathogen and establish viability of a pathogen cell (e.g. propidium iodide can be used for identifying dead cells). Cell toxicity assays can also be utilized for toxins (e.g. Toxins A and B in *Clostridium difficile* and Enterocin in VRE, etc.) based detection of pathogens. Further in case of sporulating bacteria, spore detection assays can also be utilized. In case of culturable bacteria, the viability of pathogens can even be established using culturing methods based on selective media followed by methods to detect specific pathogens discussed above. In case of an infection in living beings, observation of phenotypic effects like alleviation of infection symptoms is also within scope of this disclosure. The symptoms may vary with type of infection and may be observed by registered medical practitioner or healthcare professional. Any other method of detecting pathogens are also within scope of this disclosure. In case pathogen presence is detected, the construct can be administered again using administration module 120 and repeated till pathogen is eliminated.

In operation, a flowchart 200 illustrating the steps involved for combating infections due to antibiotic induced pathogens can be shown in FIG. 6. Initially at step 202, the sample is obtained from the infected area. At step 204, DNA is isolated and extracted from the obtained sample using one of laboratory methods. At step 206, the isolated DNA is then sequenced. Further at step 208, the presence of the antibiotic induced pathogens is detected using a plurality of detection methods, wherein the antibiotic induced pathogens comprise one or more of *Clostridium difficile*, vancomycin-resistant *Enterococcus faecalis* and vancomycin-resistant *Enterococcus faecium* from the isolated DNA of the sample.

At step 210, an engineered polynucleotide construct is prepared and administered on the infected area to combat the infections due to the antibiotic induced pathogens, wherein the engineered polynucleotide construct is comprising:
  one or more of a set of nucleotide repeat sequences with multiple copies dispersed in the of genomes of one or more of the *Clostridium difficile*, vancomycin-resistant *Enterococcus faecalis* and vancomycin-resistant *Enterococcus faecium*, wherein the set of nucleotide repeat sequences comprises one or more of a Sequence ID 001, a Sequence ID 002, a Sequence ID 003, complement of the Sequence ID 001, complement of the Sequence ID 002 or complement of the Sequence ID 003,
  a first enzyme capable of nicking and cleaving the identified set of nucleotide sequences, and
  a second enzyme capable of removal of a set of neighborhood genes flanking the set of target nucleotide repeat sequences;

Further at step 212, the efficacy of the administered engineered polynucleotide construct is checked to combat the antibiotic induced pathogens after a predefined time period. And finally, at step 214, the engineered polynucleotide construct is re-administered if the antibiotic induced pathogens are still present after checking in the infected area.

Figure 7:
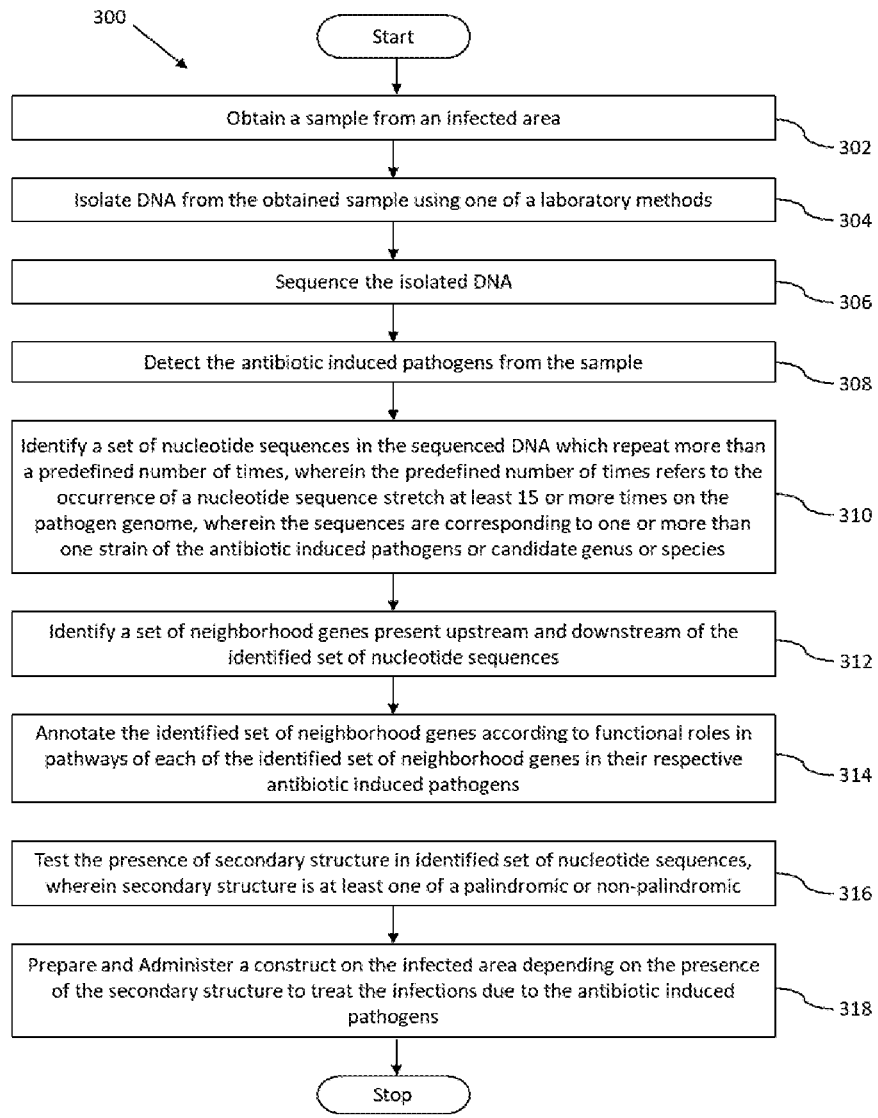
FIG. 7 is a flowchart illustrating the steps involved for combating infections due to antibiotic induced pathogens according to another embodiment of the present disclosure.

According to another embodiment of the disclosure, a flowchart 300 illustrating the steps involved for combating infections due to antibiotic induced pathogens can be shown in FIG. 7. Initially at 302, the sample is obtained from an area infected from the antibiotic induced pathogens such as *Clostridium difficile* or vancomycin-resistant *Enterococcus faecalis* or vancomycin-resistant *Enterococcus faecium*. At step 304, DNA is extracted from the sample using the pathogen detection and DNA extraction module 106. At step 306, the extracted DNA is sequenced using the sequencer 108. In the next step 308, the antibiotic induced pathogens are detected from the sample.

Further at step 310, the set of nucleotide sequences is identified in the sequenced DNA which repeat more than a predefined number of times, wherein the predefined number of times refers to the occurrence of a nucleotide sequence stretch at least 15 or more times on the pathogen genome, wherein the sequences are corresponding to one or more than one strain of the antibiotic induced pathogens or candidate genus or species, wherein the identified set of nucleotide repeat sequences occur in multiple copies at distant locations on genomes of all pathogenic strains of candidate genus or specie and these nucleotide repeat sequences do not show more than one nucleotide sequence similarity based match in genera or species other than the candidate genus or specie or within commensal strains of candidate genus or specie or within sequence of human genome. In an example, the identified set of nucleotide repeat sequences correspond to RCLOS, RENT-FL and RENT-FM in all sequenced *Clostridium difficile*, vancomycin-resistant *Enterococcus faecalis* and vancomycin-resistant *Enterococcus faecium* genomes respectively. In addition to that, the identified set of nucleotide repeat sequences are not specific to a single strain of the pathogen. At step 312, the set of neighborhood genes present upstream and downstream of the set of nucleotide repeat sequences on the genome was identified.

At step 314, the each of the identified set of neighborhood genes on the genome are annotated according to their functional roles in pathways in their respective antibiotic induced pathogens. At step 316, the presence of the secondary structure is checked in the set of nucleotide repeat sequences. The set of nucleotide repeat sequences may be palindromic in nature which may result in the formation of hairpin loops. And finally, at step 318, the construct is prepared and administered on the infected area depending on the presence of the secondary structure to treat the infection due to antibiotic induced pathogens. The administration of construct aims at targeting the set of identified nucleotide repeat sequences and removal of their flanking genes on genomes of pathogen infecting the area. The construct works in such a way that it targets multiple regions in the pathogenic genome simultaneously.

To overcome the drawbacks of the existing methods, the present system and method deals with identifying and targeting multiple copies of a stretches of nucleotide sequence occurring as repeats at distant locations on the genome as well as the important functional genes flanking these nucleotide repeat sequences. Therefore, the method allows to debilitate multiple important functions of the pathogen simultaneously. Development of resistance to the method mentioned in this disclosure is difficult as the pathogen will have to bring about multiple mutations in distant locations. The present disclosure includes targeting multiple virulence and essential proteins of antibiotic induced pathogens. The method may also include targeting various other proteins performing important functions (metabolism, host interactions, pathogenicity etc.) in pathogenic bacteria.

According to an embodiment of the disclosure, following sequences have been disclosed:

```
Sequence 001: Clostridium difficile
TNTCTC[A|G]AAAT[A|T]N[A|G][G|T]A[T|G]

AN[G|T][C|T][C|T]T[C|T]TTT

Sequence 002: Enterococcus faecium
TGTGACA[A|C]N₆TGTC[A|G]CA[A|G]N[C|T]

N[C|A]

Sequence 003: Enterococcus faecalis
T[T|C]CNN[T|C]TT[A|G][T|G]TTNT[C|T]G

G[A|G][A|G][T|C]TAAAC[A|G][G|C]T
``` where N refers to any nucleotide out of A, T, G and C and numeric values in subscript indicate the range of the number of times a nucleotide or a set of nucleotides is repeated in the sequence.

Following is the number of occurrences and locations of repeats in the strains from antibiotic induced pathogens is as follows. Due the large number of available strains, only few well characterized ones are provided below:
Occurrence of Sequence 003 corresponding to RENT-FL
*Enterococcus_faecalis*_ATCC_29212_-_
GCA_000742975.1_ASM74297v1
Number of occurrences: 15
[(12147, 12175), (180818, 180846), (367975, 368003), (719607, 719635), (886941, 886969), (925730, 925758), (973199, 973227), (1470938, 1470966), (1653359, 1653387), (1853257, 1853285), (1860181, 1860209), (1893021, 1893049), (2047943, 2047971), (2071448, 2071476), (2914106, 2914134)]
*Enterococcus_faecalis*_D32_-_
GCA_000281195.1_ASM28119v1
Number of occurrences: 19
[(97772, 97800), (340801, 340829), (562198, 562226), (649266, 649294), (806822, 806850), (972712, 972740), (1141739, 1141767), (1507289, 1507317), (1673041, 1673069), (1704427, 1704455), (1762364, 1762392), (2126742, 2126770), (2569390, 2569418), (2724035, 2724063), (2734785, 2734813), (2741709, 2741737), (2774545, 2774573), (2923465, 2923493), (2947111, 2947139)]
*Enterococcus_faecalis*_DENG1_-_
GCA_000550745.1_ASM55074v1
Number of occurrences: 17
[(347779, 347807), (859943, 859971), (901952, 901980), (1011004, 1011032), (1105884, 1105912), (1273789, 1273817), (1672476, 1672504), (1839809, 1839837), (1877084, 1877112), (1924554, 1924582), (2170754, 2170782), (2558882, 2558910), (2722158, 2722186), (2731782, 2731810), (2755134, 2755162), (2904285, 2904313), (2927834, 2927862)]
*Enterococcus_faecalis*_OG1RF_-_
GCA_000172575.2_ASM17257v2
Number of occurrences: 17
[(84734, 84762), (121250, 121278), (238021, 238049), (396287, 396315), (572320, 572348), (726309, 726337), (940215, 940243), (1127273, 1127301), (1712237, 1712265), (1728459, 1728487), (1971738, 1971766), (2338605, 2338633), (2502390, 2502418), (2679143, 2679171), (2682354, 2682382), (2705902, 2705930), (2736803, 2736831)]
*Enterococcus_faecalis*_V583__GCA_000007785.1_ASM778v1
Number of occurrences: 22

[(91710, 91738), (373131, 373159), (772923, 772951), (786064, 786092), (863504, 863532), (885335, 885363), (923385, 923413), (1091510, 1091538), (1281747, 1281775), (1658885, 1658913), (1849704, 1849732), (1884091, 1884119), (1918298, 1918326), (1974446, 1974474), (2621086, 2621114), (2796641, 2796669), (2957324, 2957352), (3008303, 3008331), (3077031, 3077059), (3157470, 3157498), (3160681, 3160709), (3184270, 3184298)]

Occurrence of Sequence 002 corresponding to RENT-FM

*Enterococcus_faecium*_Aus0085_-_GCA_000444405.1_ASM44440v1
Number of occurrences: 48
[(14356, 14382), (16475, 16501), (151783, 151809), (228076, 228102), (236260, 236286), (272981, 273007), (293925, 293951), (314342, 314368), (360282, 360308), (369990, 370016), (370357, 370383), (386668, 386694), (499524, 499550), (593771, 593797), (608059, 608085), (622787, 622813), (637054, 637080), (694992, 695018), (712939, 712965), (827267, 827293), (1063834, 1063860), (1094043, 1094069), (1283830, 1283856), (1308801, 1308827), (1379314, 1379340), (1526721, 1526747), (1750320, 1750346), (1780149, 1780175), (1810322, 1810348), (1823572, 1823598), (2047735, 2047761), (2053308, 2053334), (2153181, 2153207), (2290828, 2290854), (2351796, 2351822), (2360129, 2360155), (2377268, 2377294), (2399052, 2399078), (2519584, 2519610), (2657214, 2657240), (2765858, 2765884), (2767778, 2767804), (2786462, 2786488), (2812316, 2812342), (2922174, 2922200), (2925381, 2925407), (2967198, 2967224), (2982952, 2982978)]

*Enterococcus_faecium*_DO_-_GCA_000174395.2_ASM17439v2
Number of occurrences: 50
[(14426, 14452), (16545, 16571), (158378, 158404), (234541, 234567), (242725, 242751), (321909, 321935), (342856, 342882), (364573, 364599), (410521, 410547), (420229, 420255), (420596, 420622), (436910, 436936), (548620, 548646), (614609, 614635), (637247, 637273), (651535, 651561), (666263, 666289), (680529, 680555), (736827, 736853), (754774, 754800), (771341, 771367), (1004547, 1004573), (1050735, 1050761), (1105204, 1105230), (1231400, 1231426), (1256434, 1256460), (1323293, 1323319), (1466625, 1466651), (1642212, 1642238), (1668655, 1668681), (1700231, 1700257), (1711930, 1711956), (1957354, 1957380), (2052736, 2052762), (2072259, 2072285), (2161735, 2161761), (2216382, 2216408), (2224713, 2224739), (2241853, 2241879), (2262360, 2262386), (2329118, 2329144), (2465116, 2465142), (2574251, 2574277), (2576171, 2576197), (2593335, 2593361), (2614786, 2614812), (2625691, 2625717), (2628898, 2628924), (2670844, 2670870), (2686497, 2686523)]

*Enterococcus_faecium*_Ef_aus00233_-_GCA_900092475.1_Ef_aus00233
Number of occurrences: 46
[(14356, 14382), (16475, 16501), (172346, 172372), (248637, 248663), (256821, 256847), (349981, 350007), (370929, 370955), (391348, 391374), (437296, 437322), (447004, 447030), (447371, 447397), (463684, 463710), (577607, 577633), (673386, 673412), (687674, 687700), (702402, 702428), (716669, 716695), (774734, 774760), (792681, 792707), (866739, 866765), (1101273, 1101299), (1131480, 1131506), (1315456, 1315482), (1340442, 1340468), (1410954, 1410980), (1558440, 1558466), (1737738, 1737764), (1768241, 1768267), (1798401, 1798427), (1810099, 1810125), (2065742, 2065768), (2163792, 2163818), (2220227, 2220253), (2230082, 2230108), (2247221, 2247247), (2267728, 2267754), (2428926, 2428962), (2564944, 2564970), (2688860, 2688886), (2690780, 2690806), (2707945, 2707971), (2733802, 2733828), (2815364, 2815390), (2818571, 2818597), (2860686, 2860712), (2876377, 2876403)]

*Enterococcus_faecium*_Ef DMG1500501_-_GCA_900094185.1_Ef DMG1500501 Number of occurrences: 50
[(14351, 14377), (16418, 16444), (192484, 192510), (270276, 270302), (278460, 278486), (370902, 370928), (391847, 391873), (412263, 412289), (458200, 458226), (467908, 467934), (468275, 468301), (484582, 484608), (590589, 590615), (646655, 646681), (669292, 669318), (683577, 683603), (698301, 698327), (712561, 712587), (770367, 770393), (788311, 788337), (804866, 804892), (1040134, 1040160), (1053371, 1053397), (1084938, 1084964), (1111385, 1111411), (1293292, 1293318), (1437921, 1437947), (1511831, 1511857), (1538325, 1538351), (1728064, 1728090), (1759603, 1759629), (1995881, 1995907), (2100582, 2100608), (2120099, 2120125), (2217757, 2217783), (2275778, 2275804), (2284110, 2284136), (2301237, 2301263), (2323009, 2323035), (2327871, 2327897), (2494686, 2494712), (2633256, 2633282), (2745092, 2745118), (2747012, 2747038), (2764174, 2764200), (2791419, 2791445), (2870623, 2870649), (2873829, 2873855), (2916746, 2916772), (2932396, 2932422)]

*Enterococcus_faecium*_EFE10021_-_GCA_900066025.1_
Number of occurrences: 52
[(14356, 14382), (16424, 16450), (145336, 145362), (218985, 219011), (230144, 230170), (257019, 257045), (288003, 288029), (308757, 308783), (329298, 329324), (375545, 375571), (385502, 385528), (385869, 385895), (402177, 402203), (514162, 514188), (577262, 577288), (586361, 586387), (608737, 608763), (621730, 621756), (650426, 650452), (703634, 703660), (723285, 723311), (1031100, 1031126), (1039619, 1039645), (1068300, 1068326), (1094744, 1094770), (1278792, 1278818), (1417783, 1417809), (1484644, 1484670), (1509613, 1509639), (1635746, 1635772), (1688704, 1688730), (1743460, 1743486), (1764642, 1764668), (1941694, 1941720), (1970821, 1970847), (1988897, 1988923), (2075632, 2075658), (2130387, 2130413), (2139331, 2139357), (2151957, 2151983), (2172342, 2172368), (2177205, 2177231), (2246019, 2246045), (2379512, 2379538), (2383238, 2383264), (2491617, 2491643), (2493531, 2493557), (2532409, 2532435), (2541672, 2541698), (2544874, 2544900), (2587161, 2587187), (2602944, 2602970)]

*Enterococcus_faecium*_NRRL_B-2354_-_GCA_000336405.1_ASM33640v1
Number of occurrences: 45
[(14356, 14382), (16475, 16501), (158469, 158495), (233344, 233370), (241528, 241554), (286945, 286971), (307894, 307920), (327569, 327595), (373518, 373544), (382983, 383009), (383350, 383376), (399663, 399689), (512704, 512730), (590658, 590684), (613295, 613321), (627583, 627609), (642311, 642337), (979898, 979924), (1008544, 1008570), (1034989, 1035015), (1330740, 1330766), (1351919, 1351945), (1423051, 1423077), (1476007, 1476033), (1636935, 1636961), (1703791, 1703817), (1838490, 1838516), (1974755, 1974781), (1991317, 1991343), (2009269, 2009295), (2093585, 2093611), (2148358, 2148384), (2156937, 2156963), (2175143, 2175169), (2195405, 2195431), (2269091, 2269117), (2402537, 2402563), (2511494, 2511520), (2513414, 2513440), (2530579, 2530605), (2552152, 2552178), (2563058, 2563084), (2566265, 2566291), (2608084, 2608110), (2623862, 2623888)]
*Enterococcus_faecium*_T110_-_
GCA_000737555.1_ASM73755v1
Number of occurrences: 44
[(14356, 14382), (16475, 16501), (177624, 177650), (255097, 255123), (265882, 265908), (271707, 271733), (283909, 283935), (303821, 303847), (329716, 329742), (344678, 344704), (373329, 373355), (407288, 407314), (424010, 424036), (473519, 473545), (554036, 554062), (580717, 580743), (621665, 621691), (670099, 670125), (707691, 707717), (728166, 728192), (729559, 729585), (1070243, 1070269), (1170015, 1170041), (1186932, 1186958), (1286482, 1286508), (1288767, 1288793), (1445826, 1445852), (1483651, 1483677), (1596858, 1596884), (1600363, 1600389), (1665933, 1665959), (1699196, 1699222), (1908591, 1908617), (1944661, 1944687), (2001284, 2001310), (2212793, 2212819), (2434628, 2434654), (2508264, 2508290), (2530706, 2530732), (2597969, 2597995), (2620803, 2620829), (2623888, 2623914), (2666369, 2666395), (2682167, 2682193)]

Occurrence of Sequence 001 corresponding to RCLOS
*Clostridioides_difficile*_2007855_-_
GCA_000210455.1_ASM21045v1
Number of occurrences: 23
[(504934, 504961), (695949, 695976), (748844, 748871), (793817, 793844), (933456, 933483), (1011144, 1011171), (1074054, 1074081), (1479507, 1479534), (1656296, 1656323), (1991102, 1991129), (2005322, 2005349), (2317865, 2317892), (2394229, 2394256), (2524197, 2524224), (2734475, 2734502), (2835566, 2835593), (2865872, 2865899), (3021487, 3021514), (3257205, 3257232), (3390765, 3390792), (3460999, 3461026), (3574663, 3574690), (3682576, 3682603)]
*Clostridioides_difficile*_BI1_-_
GCA_000211235.1_ASM21123v1
Number of occurrences: 23
[(521430, 521457), (712287, 712314), (765163, 765190), (810094, 810121), (949808, 949835), (1027497, 1027524), (1090406, 1090433), (1495864, 1495891), (1672653, 1672680), (2007457, 2007484), (2021677, 2021704), (2334227, 2334254), (2410590, 2410617), (2540562, 2540589), (2750839, 2750866), (2851931, 2851958), (2882236, 2882263), (3037852, 3037879), (3245671, 3245698), (3379230, 3379257), (3449515, 3449542), (3563175, 3563202), (3671124, 3671151)]
*Clostridioides_difficile*_CD196_-_
GCA_000085225.1_ASM8522v1
Number of occurrences: 23
[(511867, 511894), (702729, 702756), (755586, 755613), (800540, 800567), (940030, 940057), (1017719, 1017746), (1080630, 1080657), (1486089, 1486116), (1662877, 1662904), (1999445, 1999472), (2013669, 2013696), (2326216, 2326243), (2402580, 2402607), (2532550, 2532577), (2742830, 2742857), (2843919, 2843946), (2874224, 2874251), (3029840, 3029867), (3237719, 3237746), (3371212, 3371239), (3441497, 3441524), (3555157, 3555184), (3663104, 3663131)]
*Clostridioides_difficile*_M120_-_
GCA_000210435.1_ASM21043v1
Number of occurrences: 23
[(816341, 816368), (849668, 849695), (864831, 864858), (997055, 997082), (1138320, 1138347), (1530005, 1530032), (1708257, 1708284), (1728403, 1728430), (2256542, 2256569), (2435642, 2435669), (2674574, 2674601), (2777553, 2777580), (2827847, 2827874), (2903028, 2903055), (2975814, 2975841), (3066619, 3066646), (3259895, 3259922), (3295093, 3295120), (3308760, 3308787), (3453808, 3453835), (3550645, 3550672), (3644990, 3645017), (3975974, 3976001)]
*Clostridioides_difficile*_BJ08_-_
GCA_001010825.1_ASM101082v1
Number of occurrences: 22
[(480659, 480686), (742332, 742359), (774271, 774298), (789476, 789503), (919736, 919763), (995999, 996026), (1059464, 1059491), (1470255, 1470282), (1985096, 1985123), (2001201, 2001228), (2406216, 2406243), (2544664, 2544691), (2624063, 2624090), (2764365, 2764392), (2815463, 2815490), (2862123, 2862150), (2890547, 2890574), (3048368, 3048395), (3450371, 3450398), (3613493, 3613520), (3623431, 3623458), (3723119, 3723146)]
*Clostridioides_difficile*_CF5_-_
GCA_000210415.1_ASM21041v1
Number of occurrences: 22
[(538093, 538120), (802691, 802718), (834832, 834859), (850036, 850063), (977657, 977684), (1053664, 1053691), (1117129, 1117156), (1522135, 1522162), (2041551, 2041578), (2055773, 2055800), (2452635, 2452662), (2591075, 2591102), (2670471, 2670498), (2810902, 2810929), (2862000, 2862027), (2908670, 2908697), (2937094, 2937121), (3095013, 3095040), (3489912, 3489939), (3643762, 3643789), (3653700, 3653727), (3753481, 3753508)]

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments of present disclosure herein address unresolved problem of antimicrobial resistance as can be observed in multi-drug resistant and extensively drug resistant pathogens. The embodiment provides a system and method to identify a nucleotide sequence stretch on a pathogen genome which occurs as a repeat at multiple distant locations on the pathogen genome. The embodiment further emphasizes that such a nucleotide repeat sequence should be specific to the pathogenic strains of target pathogen (species or genus) and should not occur more than twice within the genomes of commensal strains or in other genera. The nucleotide repeat sequence can be used to target multiple regions of pathogen genome thereby debilitating its important functions. The system involves administration of an engineered polynucleotide construct containing enzymatic machinery for binding the nucleotide repeat sequence on pathogen genome and nicking and cleaving the genome after recognition of target site.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

The invention claimed is:

1. A method for combating infections due to antibiotic induced pathogens, the method comprising:
   obtaining a sample from an infected area;
   isolating and extracting DNA from the obtained sample using one of a laboratory method;
   sequencing the isolated DNA using a sequencer;
   detecting presence of the antibiotic induced pathogens using a plurality of detection methods, wherein the antibiotic induced pathogens comprise one or more of *Clostridium difficile*, vancomycin-resistant *Enterococcus faecalis* and vancomycin-resistant *Enterococcus faecium* from the isolated DNA of the sample;
   preparing and administering an engineered polynucleotide construct on the infected area to combat the infections due to the antibiotic induced pathogens, wherein the engineered polynucleotide construct is comprising:
      one or more of a set of nucleotide repeat sequences identified and selected with multiple copies at dispersed locations on the candidate pathogen genomes of one or more of the *Clostridium difficile*, vancomycin-resistant *Enterococcus faecalis* and vancomycin-resistant *Enterococcus faecium* genomes, wherein the set of nucleotide repeat sequences comprises one or more of the sequence of Sequence ID 001, the sequence of Sequence ID 002, the sequence of Sequence ID 003, the sequence of the reverse complement of Sequence ID 001, the sequence of the reverse complement of Sequence ID 002 or the sequence of the reverse complement of Sequence ID 003,
      a first enzyme capable of nicking and cleaving the identified set of nucleotide sequences, and
      a second enzyme capable of removal of a set of neighborhood genes flanking the set of nucleotide repeat sequences;
   checking the efficacy of the administered engineered polynucleotide construct to combat the antibiotic induced pathogens after a predefined time period; and
   re-administering the engineered polynucleotide construct if the antibiotic induced pathogens are still present in the infected area post administering.

2. The method according to claim 1 wherein the samples obtained from infected area is one or more of fecal matter, blood, urine, tissue biopsy, hospital surfaces or environmental samples.

3. The method according to claim 1 wherein the DNA isolation and extraction methods comprise laboratory standardized protocols including DNA extraction and isolation kits.

4. The method according to claim 1 wherein the plurality of pathogen detection method comprises one or more of:
   a sequencing technique,
   a flow cytometry based methodology,
   a microscopic examination of the microbes in collected sample,
   a microbial culture of pathogens in vitro, immunoassays, cell toxicity assay, enzymatic, colorimetric or fluorescence assays, assays involving spectroscopic/spectrometric/chromatographic identification and screening of signals from complex microbial populations.

5. The method according to claim 1, wherein the antibiotic induced pathogens comprises one or more strains of pathogens whose occurrence can be induced by intake of antibiotics specifically pertaining to *Clostridium difficile*, vancomycin-resistant *Enterococcus faecalis* and vancomycin-resistant *Enterococcus faecium*.

6. The method according to claim 1, wherein the pathogen detection comprises one or more of sequenced microbial DNA data, a microscopic imaging data, a flow cytometry cellular measurement data, a colony count and cellular phenotypic data of microbes grown in in-vitro cultures, immunological data, proteomic/metabolomics data, and a signal intensity data.

7. The method according to claim 1 further comprising sequenced microbial data, wherein the sequenced microbial data comprises sequences obtained from sequencing platforms comprising sequences of marker genes including 16S rRNA, Whole Genome Shotgun (WGS) sequences, sequences obtained from a fragment library based sequences, sequences from a mate-pair library or a paired-end library based sequencing technique, a complete sequence of pathogen genome or a combination thereof, wherein, the pathogen detection in the sample depend on identification of taxonomic groups from these sequences.

8. The method according to claim 1, wherein the polynucleotides are inserted into vectors which allow insertion of external DNA fragments, wherein the construct is carried by plasmid or phage based cloning vectors, wherein the engineered polynucleotide construct further comprises bacteria specific promoter sequence, a terminator sequence, a stretch of Thymine nucleotides which is transcribed into a polyA tail for stabilizing the mRNAs transcripts corresponding to each enzyme, wherein the promoters and terminators specific to candidate bacteria can be utilized in the construct.

9. The method according to claim 1 wherein the engineered polynucleotide construct comprises of a CRISPR-Cas system, comprising:
 a CRISPR enzyme,
 a guide sequence capable of hybridizing to the identified target nucleotide repeat sequence within the pathogen genome,
 a tracr mate sequence, and
 a tracr sequence,
 wherein the guide sequence, the tracr mate and the tracr sequences are linked to one regulatory element of the construct while the CRISPR enzyme is linked to another regulatory module within the vector.

10. The method according to claim 1, wherein the engineered polynucleotide construct is administered using one or more of following delivery methods:
 liposome encompassing the engineered polynucleotide construct,
 targeted liposome with a ligand specific to the target pathogen on the external surface and encompassing the engineered polynucleotide construct to be administered,
 using nanoparticles like Ag and Au,
 gene guns or micro-projectiles where the construct is adsorbed or covalently linked to heavy metals which carry it to different bacterial cells, or
 bacterial conjugation methods and bacteriophage specific to the targeted pathogen.

11. The method according to claim 1, wherein the first enzyme is a nicking enzyme and the second enzyme is a cleaving enzyme.

12. The method according to claim 1, wherein the set of nucleotide repeat sequences corresponding to one or more than one strain of the antibiotic induced pathogens or candidate genus or species, wherein the set of nucleotide repeat sequences are found in multiple copies at distant locations on the genomes of all pathogenic strains of candidate genus or specie and these nucleotide repeat sequences do not show more than two nucleotide sequence similarity based match to genome sequences corresponding to genera or species other than the genome sequences of pathogens belonging to the candidate genus or species or with genomes of commensal strains within the candidate genus or specie; wherein distant locations refer to distance of greater than 10000 nucleotide base pairs.

13. The method according to claim 1 further comprising the step identifying the set of nucleotide sequences comprises:
 selecting a nucleotide sequence stretches of a predefined length Rn from the genomes of strains of candidate pathogen from the genomes of strains of candidate pathogen with a difference in the start position of two consecutive nucleotide stretches Rni+1 and Rni as 5 nucleotides, wherein the predefined length refers to the length of a stretch of nucleotide sequence picked from the complete nucleotide sequence of a bacterial genome, used as a seed input for local sequence alignment tools,
 aligning a stretch of sequences within the genome of candidate pathogen genus/specie or with genomes of all strains of the candidate pathogen genus/specie *Clostridium difficile*, vancomycin-resistant *Enterococcus faecalis* and vancomycin-resistant *Enterococcus faecium*, and
 identifying the set of nucleotide repeat sequences, repeating more than 10 times at distant locations on the bacterial genome as the set of nucleotide repeat sequences, wherein the set of nucleotide repeat sequences with repeats comprising of one or more of a Sequence ID 001, a Sequence ID 002, a Sequence ID 003, complement of the Sequence ID 001, complement of the Sequence ID 002 or complement of the Sequence ID 003.

14. The method according to claim 1, wherein the identified nucleotide repeat sequences are in genomic neighborhood of or flanking the genes encoding proteins with essential functions within a pathogen genome, wherein the genomic neighborhood refers to regions lying within a predefined number of genes to the selected nucleotide repeat sequence or the reverse complement of the selected nucleotide repeat sequence on the candidate pathogen genome or lying within a distance of predefined number of bases with respect to the selected nucleotide repeat sequence on the genome of the pathogen wherein, the important functional genes refer to the genes in pathogens which encode for proteins which are critical for survival, pathogenicity, interaction with the host, adherence to the host or for the virulence of bacteria, wherein the minimum predefined number of genes to be considered in genomic neighborhood is 10.

15. The method according to claim 1, wherein the non-culturable taxonomic groups or pathogens within a sample collected from an environment is obtained by amplification of marker genes like 16S rRNA within bacteria.

16. The method according to claim 1, wherein the information and detection of non-culturable taxonomic groups or pathogens within a sample is obtained by the binning of whole genome sequencing reads into various taxonomic groups using different methods including sequence similarities as well as several methods using supervised and unsupervised classifiers for taxonomic binning of metagenomics sequences.

17. A system for combating infections due to antibiotic induced pathogens, the system comprises:
 a sample collection module for obtaining a sample from an infected area;
 a pathogen detection and DNA extraction module isolating DNA from the obtained sample using one of a laboratory methods;
 a sequencer for sequencing the isolated DNA;
 one or more hardware processors;
 a memory in communication with the one or more hardware processors, wherein the one or more first hardware processors are configured to execute programmed instructions stored in the one or more first memories, to:
  detect presence of the antibiotic induced pathogens using a plurality of detection methods, wherein the antibiotic induced pathogens comprise one or more of *Clostridium difficile*, vancomycin-resistant *Enterococcus faecalis* and vancomycin-resistant *Enterococcus faecium* from the isolated DNA of the sample;

prepare and administer an engineered polynucleotide construct on the infected area to combat the infections due to the antibiotic induced pathogens, wherein the engineered polynucleotide construct is comprising:

one or more of a set of nucleotide repeat sequences identified and selected with multiple copies at dispersed locations on the candidate pathogen genomes of one or more of the *Clostridium difficile*, vancomycin-resistant *Enterococcus faecalis* and vancomycin-resistant *Enterococcus faecium* genomes, wherein the set of nucleotide repeat sequences comprises one or more of the sequence of Sequence ID 001, the sequence of Sequence ID 002, the sequence of Sequence ID 003, the sequence of the reverse complement of Sequence ID 001, the sequence of the reverse complement of Sequence ID 002 or the sequence of the reverse complement of Sequence ID 003, a first enzyme capable of nicking and cleaving the identified set of nucleotide sequences, and a second enzyme capable of removal of a set of neighborhood genes flanking the set of nucleotide repeat sequences;

check the efficacy of the administered engineered polynucleotide construct to combat the antibiotic induced pathogens after a predefined time period; and re-administer the engineered polynucleotide construct if the antibiotic induced pathogens are still present in the infected area post administering.

18. One or more non-transitory machine readable information storage mediums comprising one or more instructions which when executed by one or more hardware processors cause:

obtaining a sample from an infected area;

isolating and extracting DNA from the obtained sample using one of a laboratory method;

sequencing the isolated DNA using a sequencer;

detecting presence of the antibiotic induced pathogens using a plurality of detection methods, wherein the antibiotic induced pathogens comprise one or more of *Clostridium difficile*, vancomycin-resistant *Enterococcus faecalis* and vancomycin-resistant *Enterococcus faecium* from the isolated DNA of the sample;

preparing and administering an engineered polynucleotide construct on the infected area to combat the infections due to the antibiotic induced pathogens, wherein the engineered polynucleotide construct is comprising:

one or more of a set of nucleotide repeat sequences identified and selected with multiple copies at dispersed locations on the candidate pathogen genomes of one or more of the *Clostridium difficile*, vancomycin-resistant *Enterococcus faecalis* and vancomycin-resistant *Enterococcus faecium* genomes, wherein the set of nucleotide repeat sequences comprises one or more of the sequence of Sequence ID 001, the sequence of Sequence ID 002, the sequence of Sequence ID 003, the sequence of the reverse complement of Sequence ID 001, the sequence of the reverse complement of Sequence ID 002 or the sequence of the reverse complement of Sequence ID 003, a first enzyme capable of nicking and cleaving the identified set of nucleotide sequences, and a second enzyme capable of removal of a set of neighborhood genes flanking the set of nucleotide repeat sequences;

checking the efficacy of the administered engineered polynucleotide construct to combat the antibiotic induced pathogens after a predefined time period; and re-administering the engineered polynucleotide construct if the antibiotic induced pathogens are still present in the infected area post administering.

\* \* \* \* \*

SEQUENCE LISTING

```
<160> NUMBER OF SEQ ID NOS: 3

<210> SEQ ID NO 1
<211> LENGTH: 27
<212> TYPE: DNA
<213> ORGANISM: Clostridium difficile
<220> FEATURE:
<221> NAME/KEY: misc_feature
<222> LOCATION: (2)..(2)
<223> OTHER INFORMATION: n is a, c, g, t or u
<220> FEATURE:
<221> NAME/KEY: misc_feature
<222> LOCATION: (13)..(13)
<223> OTHER INFORMATION: n is a, c, g, t or u
<220> FEATURE:
<221> NAME/KEY: misc_feature
<222> LOCATION: (19)..(19)
<223> OTHER INFORMATION: n is a, c, g, t or u

<400> SEQUENCE: 1
tntctcraaa twnrkakank yytyttt                                27

<210> SEQ ID NO 2
<211> LENGTH: 26
<212> TYPE: DNA
<213> ORGANISM: Enterococcus faecium
<220> FEATURE:
<221> NAME/KEY: misc_feature
<222> LOCATION: (9)..(14)
<223> OTHER INFORMATION: n is a, c, g, t or u
<220> FEATURE:
<221> NAME/KEY: misc_feature
<222> LOCATION: (23)..(23)
<223> OTHER INFORMATION: n is a, c, g, t or u
```

```
<220> FEATURE:
<221> NAME/KEY: misc_feature
<222> LOCATION: (25)..(25)
<223> OTHER INFORMATION: n is a, c, g, t or u

<400> SEQUENCE: 2
tgtgacamnn nnnntgtcrc arnynm                                              26

<210> SEQ ID NO 3
<211> LENGTH: 28
<212> TYPE: DNA
<213> ORGANISM: Enterococcus faecalis
<220> FEATURE:
<221> NAME/KEY: misc_feature
<222> LOCATION: (4)..(5)
<223> OTHER INFORMATION: n is a, c, g, t or u
<220> FEATURE:
<221> NAME/KEY: misc_feature
<222> LOCATION: (13)..(13)
<223> OTHER INFORMATION: n is a, c, g, t or u

<400> SEQUENCE: 3
tycnnyttrk ttntyggrry taaacrst                                            28
```